(12) United States Patent
Yamamoto et al.

(10) Patent No.: US 6,252,106 B1
(45) Date of Patent: Jun. 26, 2001

(54) METHOD FOR STABILIZING A SEX PHEROMONE COMPOUND

(75) Inventors: Akira Yamamoto; Toyohisa Sakurada; Ryuichi Saguchi, all of Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 07/978,036

(22) Filed: Nov. 18, 1992

Related U.S. Application Data

(63) Continuation-in-part of application No. 07/789,291, filed on Nov. 8, 1991, now abandoned.

(51) Int. Cl.[7] ................................................. C07C 69/025
(52) U.S. Cl. ........................ 560/261; 568/417; 568/904.5; 585/5
(58) Field of Search .............................. 560/261; 568/417, 568/904.5; 585/5

(56) References Cited

U.S. PATENT DOCUMENTS 4,568,771 * 2/1986 Ishihara et al. ...................... 568/421

* cited by examiner

*Primary Examiner*—Robert Gerstl

(57) ABSTRACT

An efficient method is proposed for the stabilization of a sex pheromone compound of insect pest, which is a long-chain aliphatic unsaturated ester, alcohol, ketone or hydrocarbon compound having at least ten carbon atoms and at least one double bond in a molecule, used in pest control. The method comprises admixing the compound with 2-(2'-hydroxy-5'-methylphenyl) benzotriazole and an antioxidant which is preferably a hydroquinone compound such as tert-butyl hydroquinone, 2,5-di-tert-butyl hydroquinone and 2,5-di-tert-amyl hydroquinone.

3 Claims, No Drawings

METHOD FOR STABILIZING A SEX PHEROMONE COMPOUND

This application is a continuation-in-part-application of application Ser. No. 07/789,291, filed Nov. 8, 1991 abandoned.

BACKGROUND OF THE INVENTION

The present invention relates to a method for the stabilization of a higher unsaturated organic compound having at least one double bond in a molecule such as those compounds used in the control of insect pests by the method of mating disruption as a sex pheromone of the insect or, more particularly, to a method for the stabilization of an ester, alcohol, ketone or hydrocarbon compound having at least 10 carbon atoms and at least one double bond in a molecule.

In relation to the pest control in agriculture by using agricultural chemicals, serious problems are noted in recent years including increased resistance against chemicals acquired by the insect species and the toxicity of the chemicals against the health of the agricultural workers as well as consumers of the agricultural products due to the residual amount of the chemicals in the products. As a countermeasure for these problems, biological methods for insect pest control are now under way of intensive investigations, of which the most promising is the method of mating disruption by utilizing various kinds of chemically synthesized sex pheromone compounds as a secretion of the insect females to attract males. It is very important in this method of pest control to keep a constant rate of release of the sex pheromone compound in the field over a long period of time, for example, by the use of the sustained-release dispensers disclosed in Japanese Patent Publication No. 61-16361. In this regard, difficulties are encountered in the use of the sex pheromone compounds for the insect pests belonging to the order of Lepidoptera which are each a long-chain aliphatic compound having at least 10 carbon atoms and at least one double bond in a molecule. The presence of double bonds in such a compound is responsible for the denaturation of the compound by the reaction of oxidation, isomerization, oligomerization and the like at the double bond when the sex pheromone compound is kept under outdoor conditions.

With an object to solve this problem, a method is proposed for the stabilization of a sex pheromone compound by the admixture thereof with an antioxidant or ultraviolet absorber. For example, it is reported in Journal of Chemical Ecology, volume 14, No. 8, page 1659 (1988) that the stability of a sex pheromone compound can be improved by the addition of an antioxidant such as di-tert-butyl hydroxytoluene or tert-butyl hydroxyanisole in combination with an ultraviolet absorber such as 2-hydroxy-4-methoxy benzophenone and the like. Further, Japanese Patent Publication 63-12452 teaches that the stability of a higher unsaturated aliphatic aldehyde compound can be increased by the combined admixture of a benzophenone compound as an ultraviolet absorber with an antioxidant and a tertiary amine compound.

Although it is indeed that combined use of a specific antioxidant and a specific ultraviolet absorber synergistically contributes more to the improvement of the stability of a sex pheromone compound having a double bond in the molecular structure than in the use of either one of them alone, no quite satisfactory stabilizing effect can be obtained with any combinations of heretofore known antioxidants and known ultraviolet absorbers. Accordingly, it is eagerly desired to obtain a high stabilizing effect on various sex pheromone compounds by the combined addition of stabilizing agents.

It is proposed in U.S. Pat. No. 4,568,771 that a higher aliphatic unsaturated aldehyde compound can be stabilized against oxidation by the admixture of a tertiary amine compound, benzophenone compound, salicylate compound, benzotriazole compound or cyanoacrylate compound together with or without further admixture of an antioxidant. When the sex pheromone compound is not an aldehyde but an ester, alcohol, ketone or hydrocarbon compound, no very effective method is known for the stabilization of such a compound.

SUMMARY OF THE INVENTION

The present invention accordingly has an object to provide a very efficient method for the stabilization of a sex pheromone compound which is a long-chain aliphatic ester, alcohol, ketone or hydrocarbon compound having at least 10 carbon atoms in a molecule and at least one double bond in the molecular structure by the admixture of compounds having a stabilizing and antioxidizing effects thereon in combination to exhibit a synergistic effect.

Thus, the method of the present invention for the stabilization of a compound belonging to one of the above named classes, which is a long-chain aliphatic compound having at least 10 carbon atoms in a molecule and at least one double bond in the molecular structure, comprises: admixing the compound with 2-(2'-hydroxy-5'-methyl-phenyl) benzotriazole and a phenolic compound as an antioxidant in combination each in an amount in the range from 0.1 to 10% by weight based on the amount of the compound to be stabilized.

It is preferable, in particular, that the above mentioned phenolic compound as an antioxidant is selected from the group consisting of tert-butyl hydroquinone, 2,5-di-tert-butyl hydroquinone and 2,5-di-tert-amyl hydroquinone.

DETAILED DESCRIPTION OF THE PREFERRED EMBODIMENTS

The above described method of the invention for the stabilization of a higher aliphatic unsaturated compound, the scope of which consists in the combined admixture of a specific benzotriazole compound and an antioxidant or, in particular, a specific hydroquinone compound, has been established as a result of the extensive studies undertaken by the inventors with an object to discover a combination of stabilizing agents capable of synergistically stabilizing such an unsaturated compound even when it is not a long-chain aliphatic aldehyde compound having at least one double bond in a molecule, which is notoriously unstable to cause denaturation by the reaction of oxidation, isomerization and oligomerization at the double bond as well as the autoxidation reaction of the aldehyde resulting in the formation of a carboxylic acid or an oligomer. It has been unexpectedly discovered that the above described combination of the specific stabilizing agents has a strong stabilizing effect on the long-chain unsaturated aliphatic ester, alcohol, ketone and hydrocarbon compounds belonging to the classes of sex pheromone compounds having at least one double bond in a molecule. It is important that the specific benzotriazole compound and an antioxidant or, in particular, the specific hydroquinone compound are used in combination in order to exhibit a strong synergistic effect. If desired, other types of stabilizing agents can be used in combination with these two compounds.

The amounts of addition of these specific benzotriazole compound and antioxidant are each in the range from 0.1 to 10% by weight based on the amount of the higher aliphatic unsaturated compound. In particular, the amount of the benzotriazole compound is preferably in the range from 1 to 5% by weight based on the amount of the higher aliphatic unsaturated compound. When the amount of either one of the compounds is too small, the desired stabilizing effect cannot be fully exhibited as a matter of course while no further improvement can be obtained by increasing the amount thereof to exceed the above mentioned upper limit rather with an economical disadvantage.

Examples of the phenolic compounds as an antioxidant which can be used in combination with the specific benzotriazole compound include tert-butyl hydroquinone, 2,5-di-tert-butyl hydroquinone, 2,5-di-tert-amyl hydroquinone, 4-methoxy phenol, 2-tert-butyl-4-methoxy phenol, 3-tert-butyl-4-methoxy phenol, 2,6-di-tert-butyl-4-methoxy phenol, 2,6-di-tert-butyl-4-methyl phenol, 2,5-di-tert-butyl-3-hydroxy phenol, hydroquinone, 4,4'-methylene bis-(2,6-di-tert-butyl phenol) and the like, of which tert-butyl hydroquinone, 2,5-di-tert-butyl hydroquinone and 2,5-di-tert-amyl hydroquinone are particularly preferable in view of the high stabilizing effect on and good miscibility with the higher aliphatic unsaturated ester, alcohol, ketone or hydrocarbon compound.

The method of the present invention is applicable to any one of the ester, alcohol, ketone and hydrocarbon compounds provided that it is a long-chain aliphatic compound having at least one double bond in a molecule although the advantage obtained by the inventive method is remarkably high when the method is applied to a compound selected from the group consisting of: Z-7-dodecenyl acetate; Z-8-dodecenyl acetate; Z-9-dodecenyl acetate; E,Z-7,9-dodecadienyl acetate; E,E-8,10-dodecadienyl; E-4-tridecenyl acetate; Z-9-tetradecenyl acetate; Z-9-tetradecenol; Z-11-tetradecenyl acetate; Z,E-9,11-tetradecadienyl acetate; Z,E-9,12-tetradecadienyl acetate; Z-11-hexadecenyl acetate; Z,Z-7,11-hexadecadienyl acetate; E,E,Z-4,6,10-hexadecatrienyl acetate; Z,Z-3,13-octadecadienyl acetate; E,Z-3,13-octadecadienyl acetate; Z-13-icosen-10-one; E,E,Z-10,12,14-hexadecatrienyl acetate; E,Z,Z-4,7,10-tridecatrienyl acetate; E,Z-4,7-tridecadienyl acetate; Z,Z,Z-3,6,9-nonadecatriene; Z,Z,Z-3,6,9-eicosatriene; Z,Z,Z-3,6,9-heneicosatriene and the like. In particular, the advantage obtained by the inventive method is more remarkable when the compound to be stabilized is a long-chain aliphatic compound having two or more double bonds in a molecule such as long-chain aliphatic acetates and alcohols having a 1,3- or 1,4-dienic structure among the above named compounds.

In the following, the method of the present invention is illustrated in more detail by way of examples and comparative examples although the scope of the invention is never limited thereby in any way.

EXAMPLE

In each of the tests No. 1 to No. 20 described below, a glass capillary tube (test No. 1 to No. 5) or polyethylene capillary tube (test No. 6 to No. 20) having an inner diameter of 1 mm, outer diameter of 2 mm and length of 200 mm was filled with 100 mg of a liquid mixture of one of the higher aliphatic unsaturated compounds I to VII shown below as the test compound with 2-(2'-hydroxy-5'-methylphenyl) benzotriazole, referred to as HMBT herein-below, in an amount of 1 to 3% by weight indicated in Table 1 and one of the five phenolic compounds shown below in an amount indicated in Table 1 and kept standing outdoors as tightly stoppered to be kept outdoors and exposed to direct sun light during a period of three months starting with June in central Japan (test No. 1 to No. 5) or kept standing for three months under irradiation with a xenon lamp (test No. 6 to No. 20).

After the above mentioned three months exposure, the capillary tubes were opened and the liquid mixture taken out was subjected to the gas chromatographic analysis by the internal standard method to determine the percentage of the test compound remaining undecomposed in the respective mixtures. The results are shown in Table 1.

Higher Aliphatic Unsaturated Compounds (test compounds)

I: E,Z-7,9-dodecadienyl acetate

II: E,Z-9,11-tetradecadienyl acetate

III: E,Z-9,12-tetradecadienyl acetate

IV: Z,Z-7,11-hexadecadienyl acetate

V: E,E-8,10-dodecadienyl

VI: Z-13-icosen-10-one

VII: Z,Z,Z-3,6,9-eicosatriene

Phenolic Antioxidant Compounds

TBH: tert-butyl hydroquinone

DBH: di-tert-butyl hydroquinone

DAH: di-tert-amyl hydroquinone

BHT: di-tert-butyl hydroxytoluene

BHA: tert-butyl hydroxyanisole

TABLE 1

| Test No. | Test compound | HMBT added, % | Antioxidant added Compound | % | Undecomposed amount, % |
|---|---|---|---|---|---|
| 1 | I | 2 | TBH | 2 | 93 |
| 2 | I | 2 | BHA | 2 | 87 |
| 3 | III | 3 | TBH | 5 | 91 |
| 4 | IV | 3 | TBH | 2 | 94 |
| 5 | IV | 3 | BHT | 2 | 91 |
| 6 | I | 1 | DBH | 1 | 75 |
| 7 | I | 1 | DAH | 5 | 73 |
| 8 | I | 1 | BHT | 2 | 71 |
| 9 | II | 2 | DBH | 2 | 73 |
| 10 | II | 2 | TBH | 2 | 68 |
| 11 | II | 2 | DAH | 1 | 70 |
| 12 | II | 2 | BHT | 5 | 69 |
| 13 | III | 2 | DAH | 2 | 75 |
| 14 | III | 2 | TBH | 2 | 71 |
| 15 | III | 2 | DBH | 10 | 83 |
| 16 | IV | 1 | DBH | 0.2 | 89 |
| 17 | V | 1 | BHT | 2 | 88 |
| 18 | V | 1 | DBH | 1 | 85 |
| 19 | VI | 1 | TBH | 1 | 91 |
| 20 | VII | 2 | DBH | 5 | 67 |

COMPARATIVE EXAMPLE

The experimental procedure in each of the comparative tests No. 21 to No. 3 was substantially the same as in the preceding tests by using a glass capillary tube under exposure to direct sun light (test No. 21 to 25) or by using a polyethylene capillary tube under irradiation with a xenon lamp (test No. 26 to No. 36) except that, in some of the tests, the stabilizing agents were entirely omitted, the HMBT was replaced with one of the substitute compounds 2-hydroxy-4-methoxy benzophenone, referred to as HMBP hereinbelow, and 2-hydroxy-4-octoxy benzophenone, referred to as HOBP hereinbelow, or the phenolic antioxidant compound was replaced with one of other antioxidant compounds identified below each in an amount indicated in Table 2. The results of the tests are shown in Table 2.

Non-phenolic Antioxidant Compounds

QL: quinoline

VE: tocopherol

VEN: tocopherol nicotinate

TABLE 2

| Test No. | Test compound | HMBT or substitute compound | % added | Antioxidant added compound | % | Undecomposed amount, % |
|---|---|---|---|---|---|---|
| 21 | I | none | | none | | 8 |
| 22 | I | HMBP | 5 | BHA | 5 | 52 |
| 23 | III | none | | BHA | 5 | 54 |
| 24 | IV | none | | none | | 43 |
| 25 | IV | HMBP | 5 | TBH | 1 | 76 |
| 26 | I | HOBP | 2 | VE | 5 | 46 |
| 27 | I | HOBP | 2 | QL | 1 | 34 |
| 28 | II | HOBP | 2 | VE<br>BHT | 1<br>1 | 43 |
| 29 | II | HMBP | 2 | QL | 5 | 39 |
| 30 | II | HMBT | 2 | QL | 3 | 41 |
| 31 | III | HMBP | 2 | QL | 5 | 28 |
| 32 | III | HOBP | 2 | VEN | 5 | 33 |
| 33 | III | HMBT | 3 | VE | 5 | 36 |
| 34 | III | HOBP | 2 | QL<br>DBH | 3<br>1 | 40 |
| 35 | V | HMBP | 2 | QL | 5 | 21 |
| 36 | VII | HOBP | 2 | VE<br>BHA | 2<br>2 | 38 |

What is claimed is:

1. A method for the stabilization of a long-chain unsaturated aliphatic ester, alcohol, ketone or hydrocarbon compound having at least 10 carbon atoms and at least one double bond in a molecule, which comprises admixing the compound with 2-(2'-hydroxy-5'-methylphenyl) benzotriazole and a phenolic compound as an antioxidant each in an amount in the range from 0.1 to 10% by weight based on the amount of the long-chain aliphatic unsaturated compound.

2. The method for the stabilization of a long-chain unsaturated aliphatic ester, alcohol, ketone or hydrocarbon compound as claimed in claim 1 in which the phenolic compound as an antioxidant is selected from the group consisting of tert-butyl hydroquinone, 2,5-di-tert-butyl hydroquinone and 2,5-di-tert-amyl hydroquinone.

3. The method for the stabilization of a long-chain unsaturated aliphatic ester, alcohol, ketone or hydrocarbon compound as claimed in claim 1 in which the amount of 2-(2'-hydroxy-5'-methylphenyl) benzotriazole is in the range from 1 to 5% by weight based on the amount of the long-chain unsaturated aliphatic compound.

* * * * *